(12) United States Patent
Yildirim

(10) Patent No.: US 11,517,765 B2
(45) Date of Patent: Dec. 6, 2022

(54) HANDS-FREE SKIN TREATMENT SYSTEM

(71) Applicant: L'OREAL, Paris (FR)

(72) Inventor: Ozgur Emek Yildirim, Bellevue, WA (US)

(73) Assignee: L'OREAL, Paris (FR)

(*) Notice: Subject to any disclaimer, the term of this patent is extended or adjusted under 35 U.S.C. 154(b) by 3 days.

(21) Appl. No.: 16/731,397

(22) Filed: Dec. 31, 2019

(65) Prior Publication Data

US 2021/0196976 A1     Jul. 1, 2021

(51) Int. Cl.
*A61N 5/06*     (2006.01)
*F21V 8/00*     (2006.01)

(52) U.S. Cl.
CPC ......... *A61N 5/0616* (2013.01); *G02B 6/0008* (2013.01); *A61N 2005/063* (2013.01); *A61N 2005/0626* (2013.01); *A61N 2005/0663* (2013.01)

(58) Field of Classification Search
CPC .......... A61N 5/0616; A61N 2005/0626; A61N 2005/063; A61N 2005/0663; A61N 5/06–2005/073; G02B 6/0008; A61B 18/20–18/28
See application file for complete search history.

(56) References Cited

U.S. PATENT DOCUMENTS

| | | | |
|---|---|---|---|
| 5,766,222 A * | 6/1998 | Petit ..................... | A61N 5/0601 606/17 |
| 5,824,023 A * | 10/1998 | Anderson ............ | A61B 18/203 607/88 |
| 10,588,694 B1 * | 3/2020 | Neev .................... | A61B 18/203 |
| 2002/0173780 A1 * | 11/2002 | Altshuler ............. | A61B 18/203 606/90 |
| 2005/0177093 A1 * | 8/2005 | Barry ................... | A61N 5/0613 604/20 |

* cited by examiner

*Primary Examiner* — Jonathan T Kuo
*Assistant Examiner* — Vynn V Huh
(74) *Attorney, Agent, or Firm* — Oblon, McClelland, Maier & Neustadt, L.L.P.

(57) ABSTRACT

A system is provided for treating a skin surface of a user, comprising: at least one light emitting source configured to focus light on a specified skin region of the user, the light being configured to treat a skin condition of the user; and a controller configured to control emission of the light onto the specified skin region of the user.

10 Claims, 9 Drawing Sheets

HANDS-FREE SKIN TREATMENT SYSTEM

BACKGROUND

Field

The present disclosure relates to a system, method, and device for providing skin treatment for a user using light emitting diodes (LEDs).

Background

Acne vulgaris, or simply acne, is a skin disease characterized by, among other things, whiteheads, blackheads, papules, pustules, and nodular cysts. Treatment for acne is widely available and includes both over-the-counter and prescription products. Treatments may include topical agents such as Benzoyl Peroxide, Retinoid, including Tretinoin and Isotretinoin which influence sebum production; Keratolytic agents such as salicylic acid which accelerate cell turnover and open hair follicles; anti-inflammatories such as Dimethyl Amino Ethanol (DMAE) to reduce redness and pain associated with acne lesions; cleansing agents such as alcohols to open the infundibulum and allow free sebum exit to the skin surface; anti-spot/pigmentation agents such as ascorbic acid to prevent or treat pigmentation and color contrast on the skin, and anti-scar agents such as copper peptides to reduce the impact of scar formation from acne lesions. Further, rosacea can be treated with antibiotics, sulfur, sodium sulfacetamide, and retinoid.

It has been proposed to expose the skin to electromagnetic radiation. The electromagnetic radiation typically includes wavelengths that are absorbed by at least one chromophore present in the skin, (e.g. melanin, hemoglobin) such that the incident energy can be converted to heat. If sufficient energy is delivered and absorbed, one or more benefits such as age spot reduction, mottled hyperpigmentation reduction, wrinkle reduction, blood vasculature reduction, reduction of skin roughness, and lifting of sagging skin may be imparted to the skin.

Certain light spectrums emitted by LEDs (blue or red) are known to be therapeutic for skin treatment against maladies such as acne and are beneficial to inhibit skin aging.

The basic premise of light-based treatment is that different wavelength trigger different reactions beneath the epidermis and penetrate the skin at varying depths. Blue light is generally used to kill the bacteria that causes acne, providing an effective treatment for blackheads and whiteheads, whereas wavelengths of red light are normally used to speed up healing and stimulate collagen production, simultaneously shrinking enlarged pores and tightening the skin.

However, it is still desirable to have a convenient at-home skin treatment device that is hands free, does not require the user to stand in a fixed position for long periods of time, and may treat multiple affected areas simultaneously.

SUMMARY

According to an embodiment, a system is provided for treating a skin surface of a user, comprising: at least one light emitting source configured to focus light on a specified skin region of the user, the light being configured to treat a skin condition of the user; and a controller configured to control emission of the light onto the specified skin region of the user.

According to an embodiment, the light emitting source is coupled to a fiber optic cable, where a termination point of the fiber optic cable is configured to attach directly to the skin surface of the user at the specified skin region.

According to an embodiment, the at least one light emitting source is configured to emit blue light.

According to an embodiment, there are a plurality of fiber optic cables which are configured to be simultaneously attached to a respective plurality of skin regions of the user.

Figure 1:
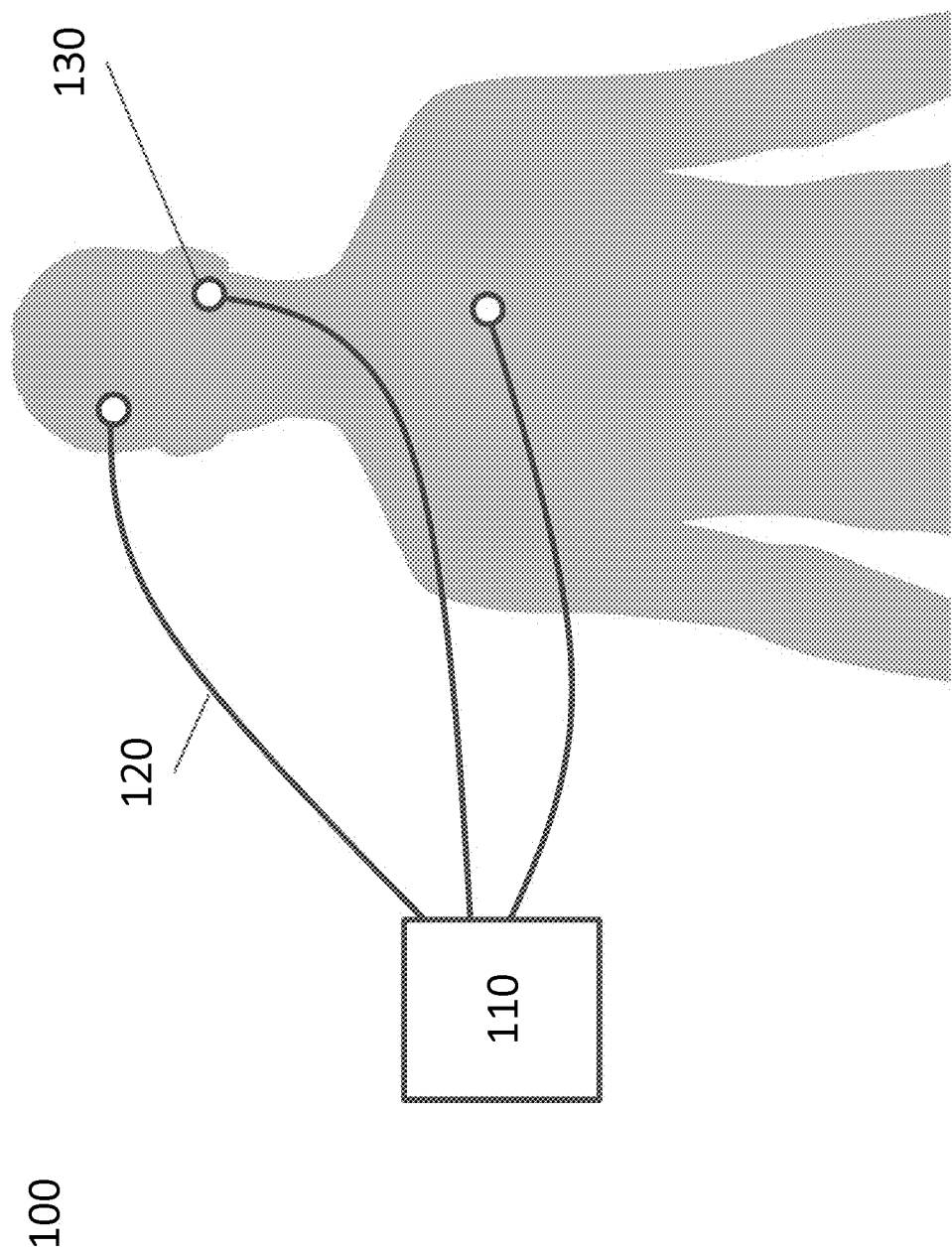
FIG. 1 is a schematic block diagram of an example system for treating a skin condition of a user according to an embodiment.

The present inventive concept is best described through certain embodiments thereof, which are described herein with reference to the accompanying drawings, wherein like reference numerals refer to like features throughout. It is to be understood that the term invention, when used herein, is intended to connote the inventive concept underlying the embodiments described below and not merely the embodiments themselves. It is to be understood further that the general inventive concept is not limited to the illustrative embodiments described below and the following descriptions should be read in such light.

Additionally, the word exemplary is used herein to mean, "serving as an example, instance or illustration." Any embodiment of construction, process, design, technique, etc., designated herein as exemplary is not necessarily to be construed as preferred or advantageous over other such embodiments. Particular quality or fitness of the examples indicated herein as exemplary is neither intended nor should be inferred.

DETAILED DESCRIPTION

FIG. 1 shows a system 100 according to an embodiment. In an embodiment, a controller (power pack) 110 has several wires 120 coming out (like tentacles) with an LED device 130 at the end. The LED can be blue only (for acne treatment), or blue+red to also help with rejuvenation/healing. The light tip has a technology to allow sticking the device onto individual acne lesions. This can be an adhesive, or a suction cup with a manual or motorized method to develop a vacuum. For instance, the suction cups may be similar to EKG suction electrodes as understood in the art. In another embodiment, the light source(s) are located in or near the main power bank, and fiber optic cables emanate from the device, delivering the light to the lesions at their free end. This free end is stuck on the individual lesions similarly. This can be an adhesive, or a suction cup with a manual or motorized method to develop a vacuum.

The type of fiber optic cable may be any known in the art, such as 50/125/250 rated fiber optic cable that is either multimode or single-mode.

Additionally, the controller 110 may have a form factor in which it can fit into user's pocket or attach to a belt or waistband of the user. The fiber-optic cables may be designed to fit under the user's clothes if desired, especially if treatment is performed on the torso or other non-facial regions of the user.

Figure 2:
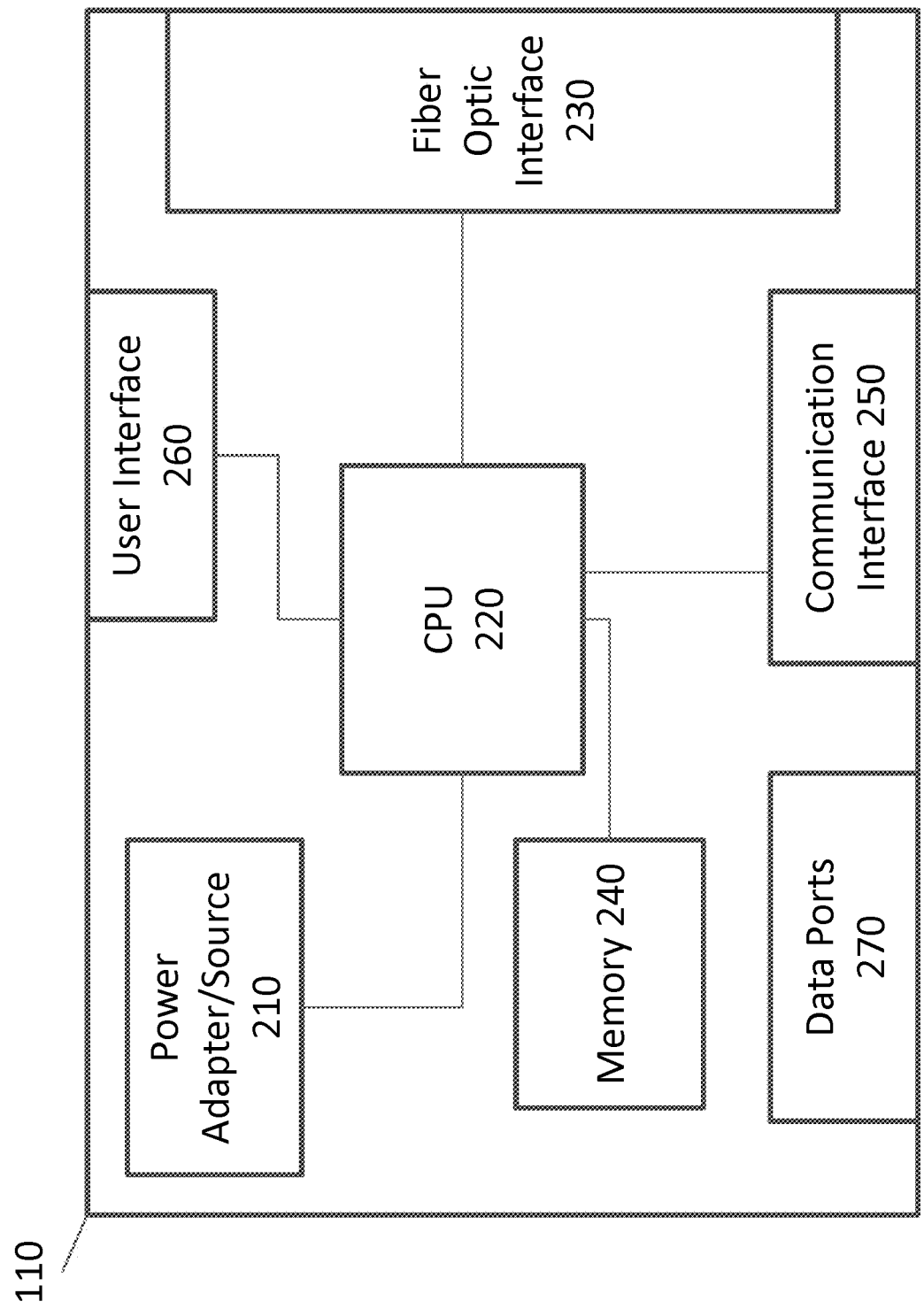
FIG. 2 is a hardware diagram of a controller according to an embodiment.

FIG. 2 shows a hardware diagram of the controller 110. In this example, a power adapter/source 210 receives external power, such as AC power from a conventional wall socket or outlet, or is a battery power supply.

In an example, the communication interface (I/F) 250 can include circuitry and hardware for communication with an external client device, which will be described later. The communication interface 250 may include a network controller such as BCM43342 Wi-Fi, Frequency Modulation, and Bluetooth combo chip from Broadcom, for interfacing with a network. The hardware can be designed for reduced size. For example, the processor 220 may be a CPU as understood in the art. For example, the processor may be an APL0778 from Apple Inc., or may be other processor types that would be recognized by one of ordinary skill in the art. Alternatively, the CPU 220 may be implemented on an FPGA, ASIC, PLD or using discrete logic circuits, as one of ordinary skill in the art would recognize. Further, the CPU may be implemented as multiple processors cooperatively working in parallel to perform the instructions of the inventive processes described above.

In an embodiment, the controller includes a user interface 260, which may be in the form of input buttons on the housing of the tool, or it may be in the form of a contact-sensitive display, such as a capacitive or resistive touch screen display.

The controller may further include a number of data ports 270, including USB data ports, DVI ports, and optical ports. In various embodiments of the present invention, fewer, more, and other types of data ports may be included. These ports may be wired electronic data ports, fiber-optic data ports, wireless data ports, or other types of data ports. Data may be received and transmitted at one or more of these ports.

A memory 240 stores software for controlling the controller, or for storing user data or other information.

The fiber optic interface 230 includes one or more light sources for providing light to the fiber optic cables and will be discussed in more detail in FIGS. 3A-3B below.

Figures 3A, 3B:
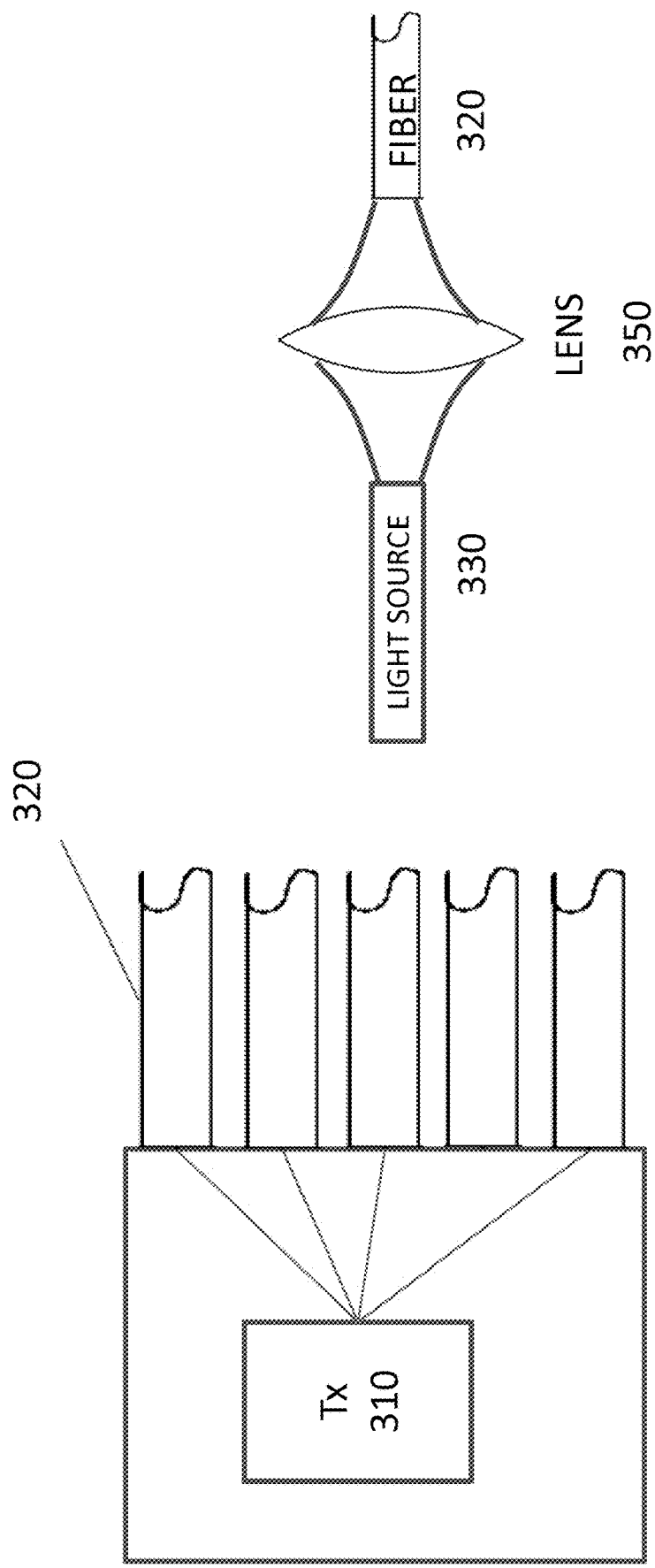
FIGS. 3A and 3B show details regarding a fiber optic interface according to an embodiment.

FIGS. 3A and 3B show details regarding the fiber optic interface 230. FIG. 3A shows that when transmitter 310 transmits data, transmitter 310 provides data to each of one or more fiber-optic lines 320 coupled to the interface. As many fiber-optic lines 320 may be provided as necessary based on power or light emission requirements.

FIG. 3B shows the specific coupling of a light source 330 to the fiber optic cable 320 in the case of a single fiber optic cable. In this case the light source 330 is a light emitting diode (LED), which may be blue or red. The wavelength for blue light to have an anti-acne effect is in 400-440 nm range. For anti-aging or anti-inflammatory effect, yellow-red and infrared light in the range of 580 nm to 880 nm may be used.

Any combination of one or more light sources and fiber optic cables may be used to achieve any combination of colors or power to be emitted at the termination point of the fiber optic cable. A nominal spot size may be about 1 cm diameter in one example. If desired, a focusing attachment (see 370 in FIG. 3C) may be used to reduce the spot size to around 0.5 cm while also increasing areal intensity for more targeted treatment on a lesion 360 on a user's skin shown in FIG. 3C. Similarly, for "raised" lesions (365, FIG. 3D), an attachment 380 may be used (FIG. 3D) to have a hemispherical cavity in it for the lesion to be covered without having to press it down flat. The device attaches to the skin around its perimeter (ring) but the light is delivered to the lesion from the hemispherical dome.

Figure 3D:
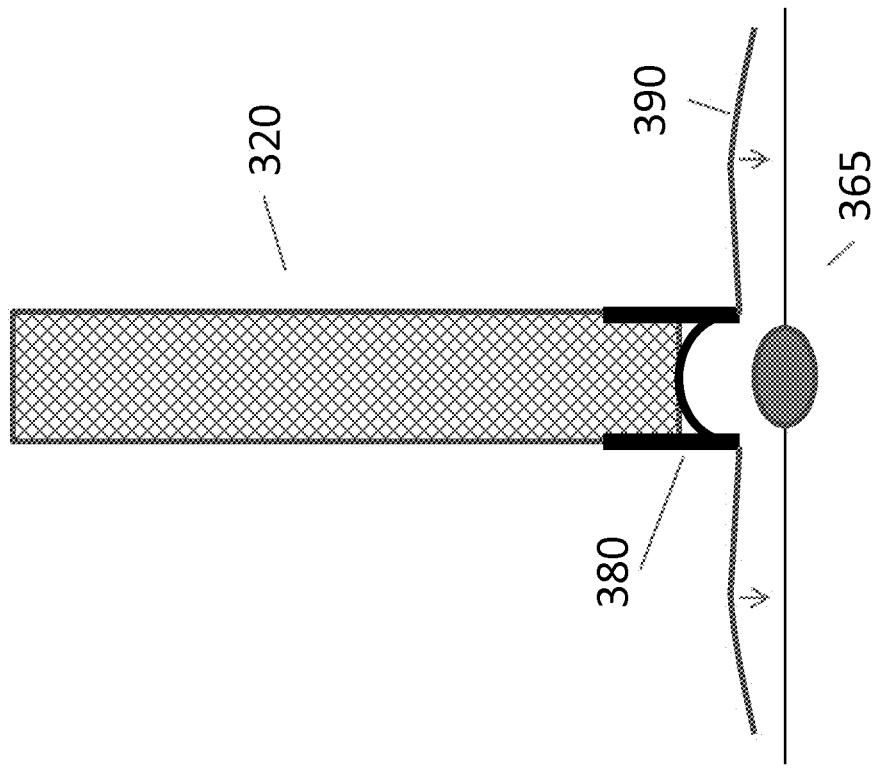
FIGS. 3C and 3D show details regarding a termination point of a fiber optic cable upon a user's skin region.
Figure 3C:
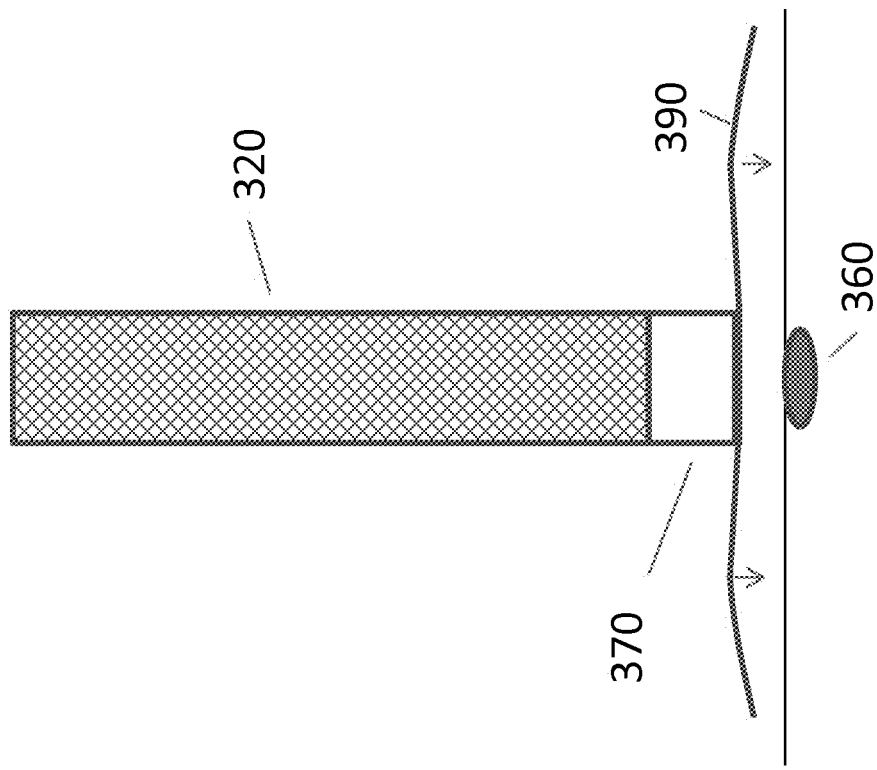

The delivery tip can be attached to the skin via an adhesive "skirt" such as element 390 shown in FIGS. 3C-3D. This skirt, kind of like a ring shaped tape that is sticky on one side, can be a disposable consumable.

While FIG. 3A shows a transmitter 310 to transmit data, the fiber optic cable 320 is not intended to be used to communication information data to a receiver. However, pulses of light or continuous light may transmitted over the fiber optic cable, and therefore, the transmitter 310 may still modulate a data signal representing pulses of light or a continuous light as desired.

Figure 4:
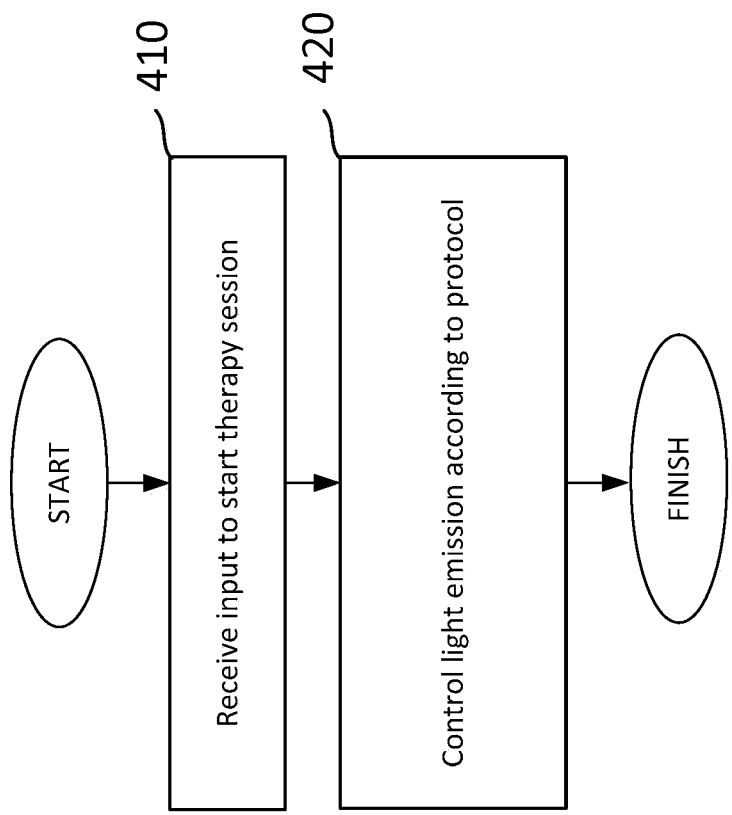
FIG. 4 shows a process performed by the system according to an embodiment.

FIG. 4 shows a process that is controlled by the controller. In step 410, an input is received at the controller 110 to start a therapy session. The session may be completely manually set by the user at the user interface 260 of the controller 110. For instance, settings of time duration, color, and power, may be set by the user for each fiber optic cable being used. Alternatively, a predetermined regimen or protocol may be a started by an input received at the controller 110, or via an external client device (such a smartphone) as described below. In step 420, the light emission at the termination point of each of the fiber optic cables is started according to the settings adopted for the session.

Figure 5A:
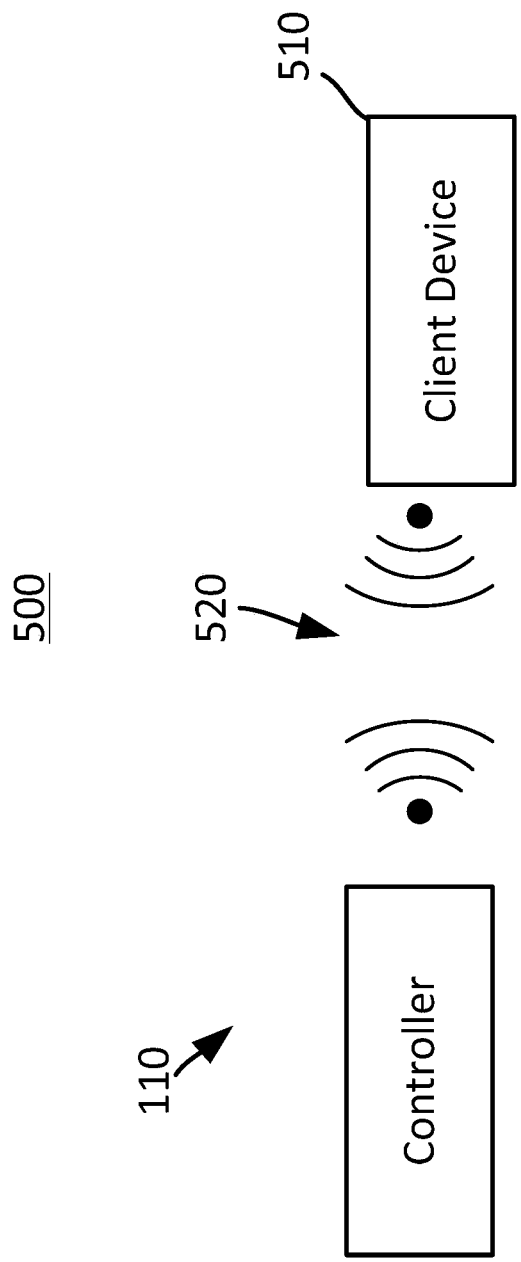
FIGS. 5A-5C show examples in which a client device and other devices interact with the controller according to an embodiment.

FIG. 5A shows a system 500 that includes the controller 110 and a client device 510. In an embodiment, the controller 110 is in communication with the client device 501 with a wireless signal 520. In an embodiment, the client device 510 is configured to operate a software application or set of software modules to receive and send communications from and to the controller 110. In an example, the software application can send a protocol or target profile to the controller 110, as well as receive data from the controller 110 to track the usage in real time.

Figure 5B:
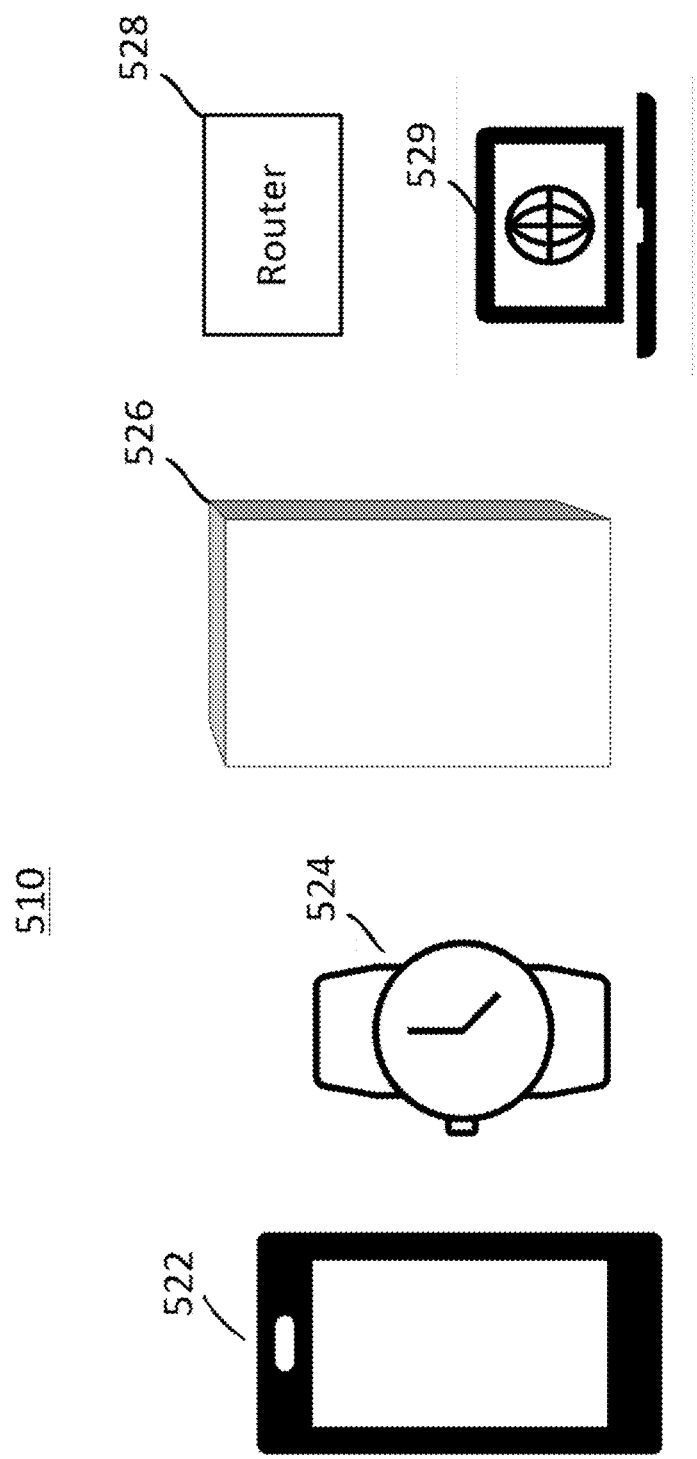

FIG. 5B shows different examples of the client devices 120 including, a mobile device 522, a wearable electronic 524, a television or magic mirror 526, a network router 528, and a personal computer 529.

The wireless signal 520 can be any appropriate signal such as an electromagnetic signal including WIFI, Bluetooth, near-field, or any other signal such as optical, and acoustic. Each client device, including the appliance, may communicate with each other through an internet connection via an 802.11 wireless connection to a wireless internet access point, or a physical connection to the internet access point, such as through an Ethernet interface. Each connected device is capable of performing wireless communication with other devices, such as through a Bluetooth connection or other wireless means as well.

Figure 5C:
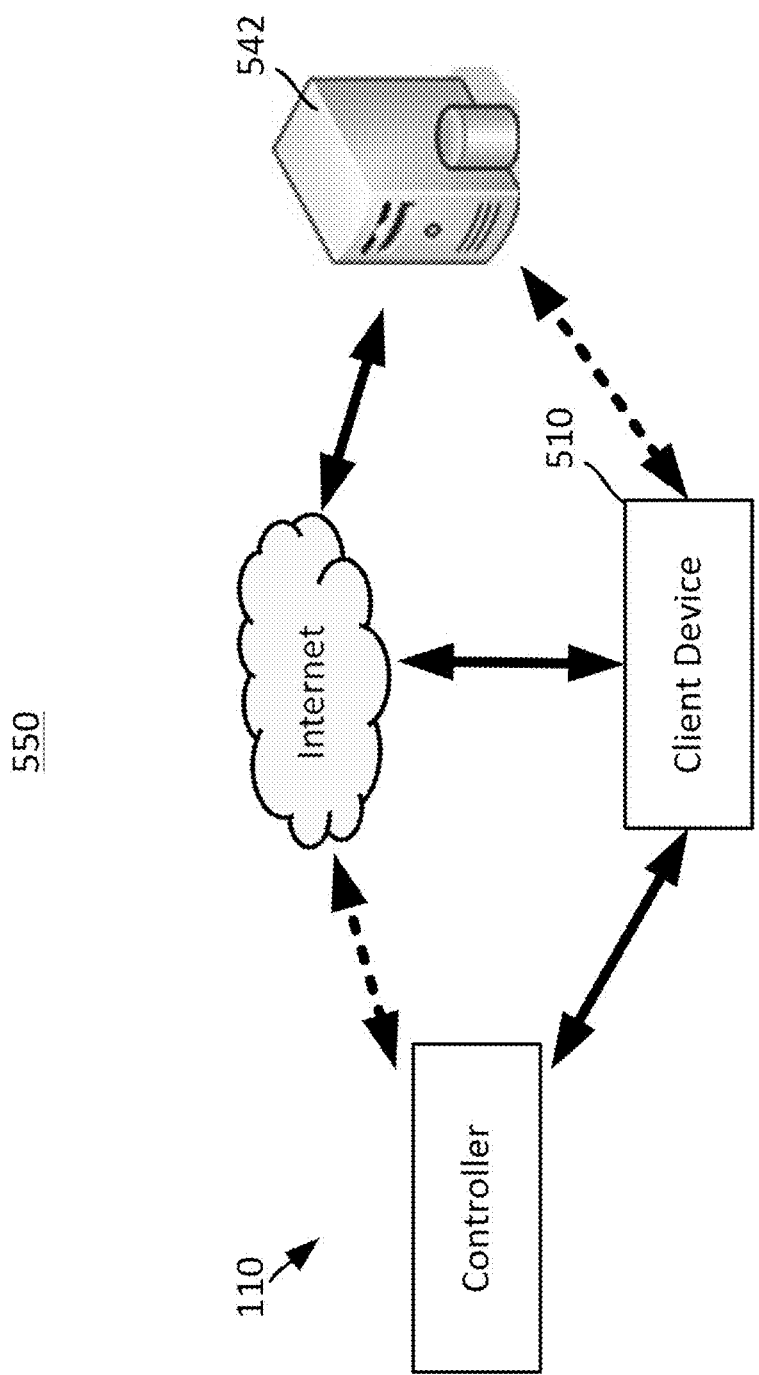

FIG. 5C is a diagram representing an example of a system 550 to promote optimum performance of a controller 110, according to one example. The system 550 includes at least the controller and the client device. Optionally, the system 550 may further include one or more external servers 542 which are implemented as part of a cloud-computing environment and in communication with the system 550 through the Internet. The one or more external servers 542 can store user data, products such acne treatment products, cosmetic products, protocols and routines, tutorials, as well as other $3^{rd}$ party services according to an example.

The user interface or the client device can display tutorials on how to use the system 100. The user interface can create and download protocols for a regimen or routine. The user interface can coach, track usage and compare the tracked usage to the protocol, the regimen, and the routine. The user interface can calculate a score based on the tracked usage. The user interface can store the scores and the tracked usage of the system 100 in memory of the client device. The user interface can be used to make a purchase of any products related to the system 100. For instance, the system 100 may be used with a combination of acne treatment products used for treating the user's acne or skin condition, and the client device can output recommendations on products to be used, and which step in the process they are to be used.

In addition to using the tutorials, the user may connect the client device 510 with the system 100 over the wireless connection (such as the Bluetooth or Wi-Fi connection) to receive real-time feedback while using the system, or to record the usage of the system for later reporting or feedback.

For example, the system 100 can communicate what settings are currently being used at the system 100.

The client device can also have a camera function that can be used to provide inputs to the customer profile. For instance, the camera can take images of the user's skin to determine if treatment is possible, or to make further recommendations to the user based on the characteristics or color of the skin.

The client device is configured to upload data regarding the user to an external system or server (such as a cloud-based system). Such data may include the user profile, amount of use of the system 100, or performance results when using the system 100. The client device can also provide an option to keep the user data anonymous.

Furthermore, the circuitry of the client device may be configured to actuate a discovery protocol that allows the client device and the system 100 to identify each other and to negotiate one or more pre-shared keys, which further allows the system 100 and the client device to exchanged encrypted and anonymized information. The discovery protocol may further allow the client device and system to exchange treatment regimen information.

The client device can use the camera function to provide a sharing feature, in which the user can upload photos taken before and/or after the use of the system. The uploaded photos can be used for receiving feedback from professional hair stylists or other users. In an embodiment, the uploaded photos may be uploaded directly to a social media platform.

Figure 6:
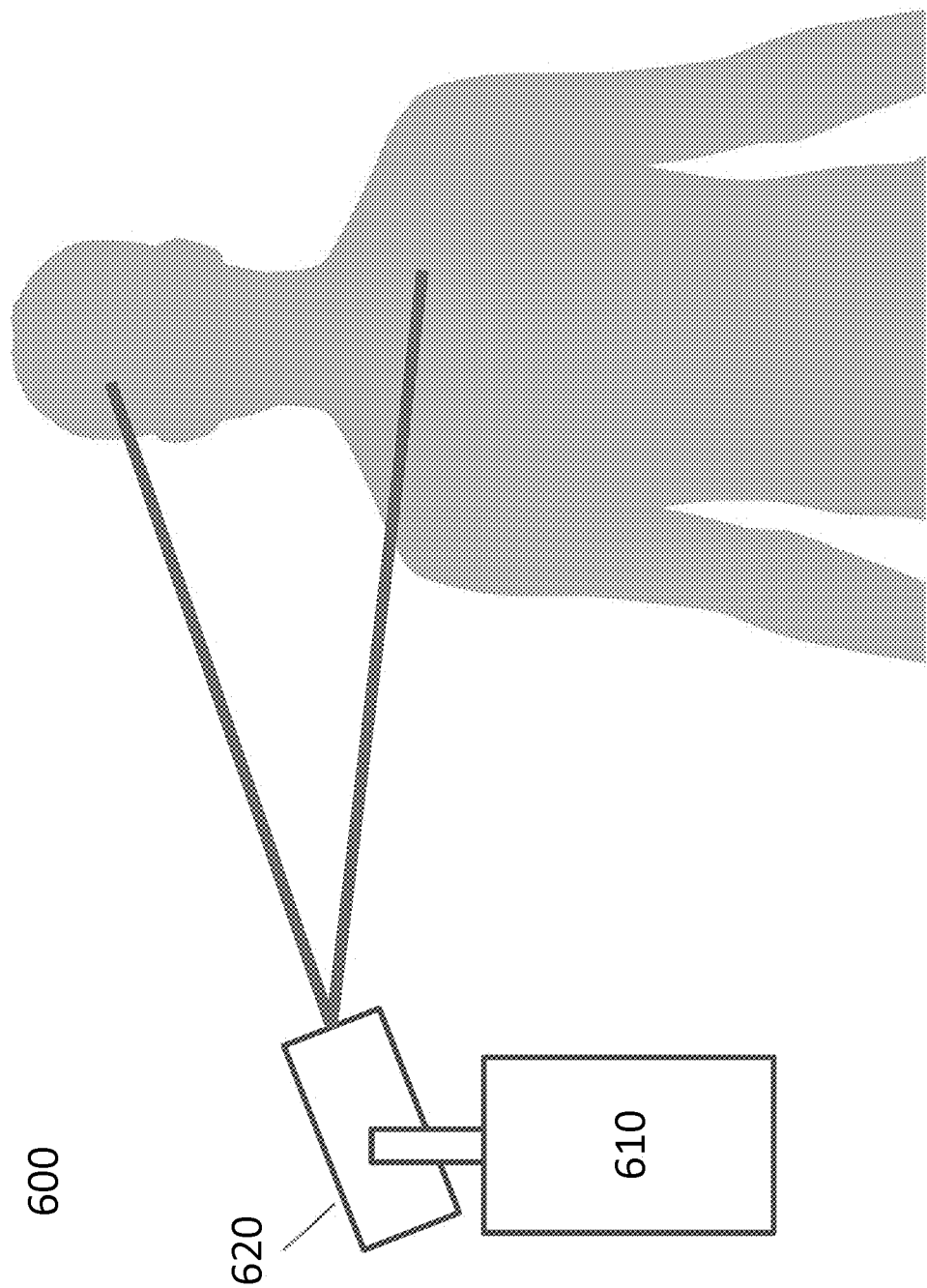
FIG. 6 shows a non-contact system for treating a skin condition according to an alternative embodiment.

FIG. 6 shows a second embodiment of a system 600 for treating a skin condition using light therapy. In the system 600, fiber optic cables are not used, and light is emitted from a light emitter device 620 that is coupled to the controller 610. System 600 represents a hands-free desktop non-contact acne treatment device that may emit steerable blue light known to be effective in acne treatment. For example, the blue light can be a laser beam that is steered to track and shine on the acne lesions. Alternatively, the source can be a non-collimated source such as an LED, and be used in conjunction with suitable optics to focus the light on the lesion.

In a specific example, the light emitter device 620 may include collimated light or focusing optics to provide a desired energy and intensity of the light at the target point(s) on the skin surface of the user, while remaining at a safe level of energy or intensity. While the user may stay still during the therapy session using the system 600, the controller 610 may be configured to utilize an on-board camera sensor (not shown) to dynamically track the user as the user moves.

The on-board camera in system 600 may further be configured to track the face or body of the user and identify legions prior to a therapy session. Feedback from the user may aid in providing machine learning to the system 600 to help the system correctly identify lesions or acne for future use.

The system 600 is shown separately and distinct from the system 100 of FIG. 1. However, the two systems may be combined into a single system which provides all of the features of both systems in a single device.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit", "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be, for example, but is not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a solid state disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, a phase change memory storage device, or any suitable combination of the foregoing. In the context of this document, a computer readable storage medium may be any tangible medium that can contain, or store a program for use by or in connection with an instruction execution system, apparatus, or device.

Computer program code for carrying out operations for aspects of the present invention may be written in any combination of one or more programming languages, e.g., an object oriented programming language such as Java, Smalltalk, C++ or the like, or a conventional procedural programming language, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). It is to be understood that the software for the computer systems of the present invention embodiments may be developed by one of ordinary skill in the computer arts based on the functional descriptions contained in the specification and flow charts illustrated in the drawings. Further, any references herein of software performing various functions generally refer to computer systems or processors performing those functions under software control.

The computer systems of the present invention embodiments may alternatively be implemented by any type of hardware and/or other processing circuitry. The various functions of the computer systems may be distributed in any manner among any quantity of software modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.).

The foregoing examples are illustrative of certain functionality of embodiments of the invention and are not intended to be limiting. Indeed, other functionality and other possible use cases will be apparent to the skilled artisan upon review of this disclosure.

What is claimed is:

1. A system for treating a skin surface of a user, comprising:
   at least one light emitting source configured to focus light on a specified skin surface region of the user, the light being configured to treat a skin condition of the user; and
   a controller configured to control emission of the light onto the specified skin surface region of the user,
   wherein the at least one light emitting source is coupled to a fiber optic cable, where a flat termination point of the fiber optic cable is coupled to an attachment that is configured to attach directly to the skin surface of the user at only a perimeter of the specified skin surface region, the perimeter corresponding to a bottom of a hemispherical dome within the attachment, where the flat termination point of the fiber optic cable is at the top of the hemispherical dome with a hemispherical cavity formed between the fiber optic cable and the bottom of the hemispherical dome, and the attachment includes a ring-shaped adhesive element that is configured to attach to the skin surface of the user at an area surrounding the perimeter.

2. The system according to claim 1, wherein the at least one light emitting source is configured to emit blue light.

3. The system according to claim 1, wherein there are a plurality of fiber optic cables which are configured to be simultaneously attached to a respective plurality of skin regions of the user.

4. The system according to claim 1, wherein the at least one light emitting source configured to focus collimated light on the specified skin surface region of the user.

5. The system according to claim 1, wherein the at least one light emitting source is a light emitting diode (LED) and the system further includes a focusing optical element to focus the light on the specified skin surface region of the user.

6. The system according to claim 1, wherein the at least one light emitting source is configured to focus pulses of light on the specified skin surface region of the user.

7. The system according to claim 1, wherein the at least one light emitting source is configured to focus continuous light on the specified skin surface region of the user.

8. The system according to claim 1, wherein the controller is configured to control settings of time duration, color, and power for the at least one light emitting source to focus the light on the specified skin surface region of the user in accordance with a predetermined regimen or protocol.

9. The system according to claim 1, wherein the at least one light emitting source is configured to focus the light to have a spot size between 0.5 cm and 1 cm on the specified skin surface region of the user.

10. The system according to claim 1, wherein the ring-shaped adhesive element is a disposable consumable product.

* * * * *